United States Patent [19]

Schlüter

[11] Patent Number: 4,973,450

[45] Date of Patent: Nov. 27, 1990

[54] DEVICE FOR URINALYSIS

[75] Inventor: Gert Schlüter, Gundelfingen, Fed. Rep. of Germany

[73] Assignee: Hoyer GmbH and Company, Fed. Rep. of Germany

[21] Appl. No.: 199,285

[22] Filed: May 26, 1988

[30] Foreign Application Priority Data

Jun. 10, 1987 [DE] Fed. Rep. of Germany ....... 3719302

[51] Int. Cl.$^5$ .............................................. G01N 1/10
[52] U.S. Cl. .................................... 422/101; 422/100;
422/68.1; 422/81; 422/102; 436/63; 436/178;
436/180; 73/863.23; 73/863.83; 73/864.34;
73/864.83
[58] Field of Search ................... 422/100, 101, 68, 81,
422/102; 436/178, 180, 63, 85, 124, 177;
73/863.63, 864.83, 863.23, 864.21, 864.34

[56] References Cited

U.S. PATENT DOCUMENTS

| | | | |
|---|---|---|---|
| 3,512,940 | 5/1970 | Shapiro | 422/101 |
| 3,846,077 | 11/1974 | Ohringer | 422/101 X |
| 4,533,643 | 8/1985 | Bell et al. | 422/101 X |

Primary Examiner—Robert J. Warden
Assistant Examiner—Lynn M. Kummert
Attorney, Agent, or Firm—Browdy and Neimark

[57] ABSTRACT

A device for urinalysis, in particular for microscopic quantitative analysis of urinary sediment, consists of a cylindrical specimen container with an opening at the top and a pipette tip at the bottom end, a tubular plunger inserted into this specimen container and moveable therein in a leakproof manner, both parts consisting of transparent material, a stopper for the specimen container at the top end and a sealing cap for the pipette tip, a single-stage or multi-stage filter arrangement being located in the plunger close to the bottom end.

5 Claims, 2 Drawing Sheets

DEVICE FOR URINALYSIS

BACKGROUND OF THE INVENTION

1. Field of the Invention

The invention relates to a device for urinalysis and in particular for the examination of urinary sediments.

2. Description of the Prior Art

In order to detect pathological processes in the urinary tract and to diagnose them in the early stages, so-called sediment analysis has been carried out for a long time. This principally involves microscopically detecting and evaluating pathological constituents from the urinary sediment, in order to be able to take appropriate therapeutic measures.

Erythrocytes and leukocytes are present in very small quantities in the urine of healthy subjects. An increase in these blood cells above experimentally determined limit values then provides an indication of inflammatory processes or other disorders. However, other cell types may also additionally be present in the urine, for example renal epithelial cells, urothelial cells of various types and also, in the urine from females, squamous epithelia. There are also casts, crystals, bacteria and others. Since these constituents are present in a varying liquid volume depending on the concentration, a drop of urine taken directly from a total specimen does not provide any quantifiable result under the microscope because, in general, the dilution factor is too high. A quantitative statement in addition to a morphological examination is only possible if an accumulation of the particles in the liquid takes place. A calculation of the number of the particular cells per ml of urine is only possible if the accumulation or concentration takes place exact and standardized.

For such an accumulation, a centrifugation has hitherto been used with, for example, 10 ml of urine being centrifuged at 2,000 g. A supernatant of 9 ml is then decanted off and the sediment is resuspended in 1 ml of residual urine. This suspension is then filled into a counting chamber, for example a Fuchs-Rosenthal chamber, which holds a defined amount of liquid. The particles are deposited in this on a grating of defined surface division and, following morphological classification, they are counted under the microscope per surface unit and extrapolated to 1 ml of urine.

It is known that cell losses of up to 40% occur during centrifugation, particularly in the case of epithelial cells.

The decanting-off is also associated with considerable errors, since the techniques required for this demand a certain manual dexterity.

SUMMARY OF THE INVENTION

All in all, the previous methods for concentrating the sediment particles to a smaller liquid volume are not satisfactory, and the invention is accordingly based on the object of providing a device for concentrating the original liquid volume to a defined fraction, and of making possible a subsequent low-error counting of the individual particles under the microscope.

The device achieving such an object should make it possible to simply, quickly and cleanly remove a particular, defined amount of urine from a specimen container, and subsequently to concentrate the withdrawn suspension to a predetermined fraction, preferably to a tenth. A drop from this concentrated amount of liquid should then be introduced into a counting chamber.

To achieve this object, a device is proposed which has a cylindrical specimen container of transparent material, preferably synthetic material, of which one end, at the top during use, is open and can be sealed in a leakproof manner by a stopper, and of which the other end at the bottom is designed tapered in a funnel shape and empties into a pipette tip, which device furthermore has a stopper with an elastically deformable end wall for the specimen container and also a sealing cap which can be attached to the pipette tip and seals the latter in a leakproof manner, which device furthermore includes a tubular, cylindrical plunger of transparent material, preferably synthetic material, which can be inserted liquid-tight and gas-tight into the specimen container and is slideable in the latter, and of which the top, open end can be sealed in a leakproof manner by a stopper, and of which the bottom end, likewise open, is sealed by a filter arrangement, a measuring mark being provided on the circumference of the specimen container at "10 ml", and the device having a cylinder of a transparent material, preferably synthetic material, arranged inside the plunger, connected in a leakproof manner to the top of the filter arrangement and forming a backflush chamber, which cylinder is sealed at the top by an end wall with a very fine centre bore.

It is furthermore proposed that a disc projects radially outwards from the pipette tip of the specimen container and that the sealing cap is provided with a rolled edge which, when pushed onto the pipette tip, turns inwards and clamps the sealing cap on the disc.

In a development of the invention it is proposed that the filter arrangement has two filters connected in series and of different pore size.

In addition, a third filter is preferably also provided which has a larger pore size than the two above-mentioned filters.

Finally, it is proposed that between the first two filters and the third filter there is a cylindrical tube support which forms a second backflush chamber.

BRIEF DESCRIPTION OF THE DRAWINGS

The device is described in greater detail below in an exemplary embodiment, with reference to the drawing in which.

DETAILED DESCRIPTION OF THE INVENTION

Figure 1:
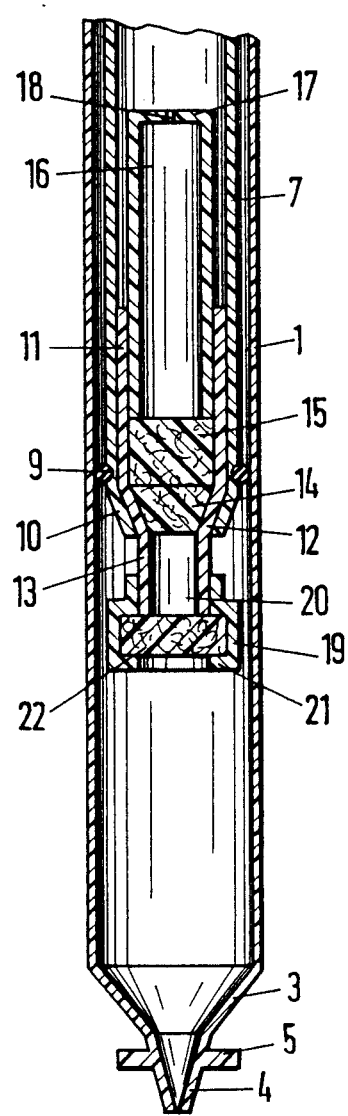
FIG. 1 shows a section through a device according to the invention consisting of specimen container and inserted plunger with filter device and backflush chamber.

The device shown in FIG. 1 comprises a cylindrical specimen container 1 with an upper flange 2, a bottom, funnel-shaped tapered end 3, a pipette tip 4 connected to it and, projecting outwards from this tip, a disc 5 whose purpose will be explained below.

On the outer casing of the specimen container 1 there is a measuring mark (not shown) for 10 ml.

A cylindrical, tubular plunger 7 is inserted into the specimen container 1, which plunger also has, at its top, open end, an outwardly directed flange 8.

Close to its bottom end this plunger 7 has, on its circumference, a sealing ring 9 of soft rubber. The plunger is smoothly slideable inside the specimen container, but with the sealing ring 9 ensuring liquid-tight and air-tight sealing.

The plunger 7 is slightly tapered at its bottom end at 10. A likewise conically tapered part 12 of a tube piece 11, cylindrical in its upper part and inserted into the plunger 7, is supported on this funnel-shaped taper. Below the funnel-shaped taper, this tube piece continues in a short cylindrical part 13.

The tube piece 11 serves for holding a two-part filter device consisting of the individual filters 14 and 15. One of these two filters is more closely meshed than the other. In this connection, the narrower-mesh filter piece can be fitted either below or on top.

The upper filter piece 15 is held by a cylinder 17 pushed into the tube piece 11 from above. This cylinder has, at its top end, a transverse wall with a fine center bore 18 and delimits an inner space 16 which is described as the backflush chamber. The opening 18 is maintained so small that liquids of the type concerned here, that is to say urine, cannot run out automatically when a cylinder 17 filled with this is inverted, but are instead held securely as a result of capillary action.

Below the cylindrical part 13, in a cap 19 pushed on and with a punctured base 21, there is a further filter piece 22.

By means of this combination of different filters in connection with the upper backflush chamber 16 and the lower backflush chamber 20, the concentration, which is described below, can be carried out particularly advantageously.

The individual filter pieces 15, 14 and 22 preferably consist of fibres of cylindrical cross-section, either of synthetic material, such as polyamide or polyester, or also of glass. These fibres are pressed and compacted with addition of a binding agent, which does not however fill all the cavities, and the entire fibre bundle is additionally saturated in a final immersion process with a further synthetic material.

It should also be mentioned that the specimen container 1 and also the plunger 7 and the cylinders 11 and 17 were produced from a transparent synthetic material.

Figure 2:
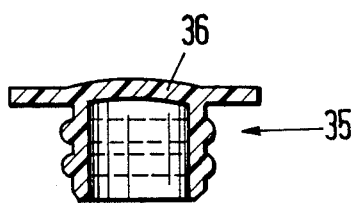
FIG. 2 shows a stopper for the specimen container after removal of the plunger.

The stopper 35 shown in FIG. 2 is used for sealing the open, top end of the specimen container 1 inside its flange 2, and possesses the following peculiarity: The middle part of this stopper is arched upwards and kept so thin that the stopper 35, consisting of a flexible synthetic material, allows this middle wall 36 to be pressed in. The purpose of this is described below.

Figure 3:
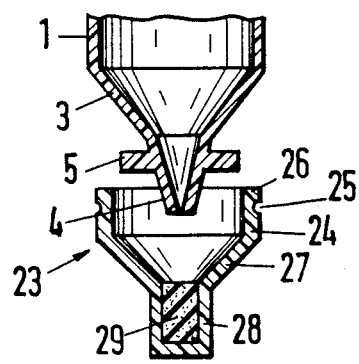
FIG. 3 shows the bottom end of the specimen container and a sealing cap provided for it.
Figure 4:
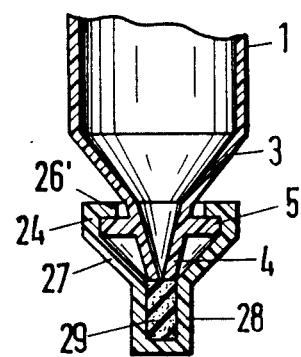
FIG. 4 shows a representation according to FIG. 3 with the sealing cap attached and clamped.

FIGS. 3 and 4 show the sealing cap 23 for the tip 4 at the bottom end of the specimen container 1, in the detached state in FIG. 3 and in the attached state in FIG. 4.

As can be seen, this cap, at its upper edge, consists of two annular parts 24 and 26 with an intermediate outer groove 25, and in such a way that, when the sealing cap is attached, the upper annular part 26 turns inwards into the position 26' shown in FIG. 4, and secures the sealing cap, in the manner of a rolled-on closure on the tip 4 and funnel-shaped end 3 of the specimen container 1.

In order to seal, in a leakproof manner, the tip 4 which is open at the bottom in this position (FIG. 4), a sealing stopper 29 of soft rubber is located in a cylindrical pocket 28 of the sealing cap.

The procedure with this device consists of the following steps:

(a) inserting the plunger 7 into the specimen container 1 with the sealing cap 23 detached;
(b) sealing the plunger 7 with the stopper 35;
(c) dipping the tip 4 of the specimen container 1 into a previously vortexed urine sample;
(d) withdrawing the plunger 7 until the top surface of the urine drawn in reaches the "10 ml" mark of the specimen container 1;
(e) sealing the tip 4 of the specimen container 1 by means of the sealing cap 23 and removing the stopper 35 from the top end of the plunger 7;
(f) slowly and steadily inserting the plunger 7 right into the specimen container 1;
(g) inverting the specimen container 1 with inserted plunger 7 once, in order to pour off the excess urine which is discarded, and then inverting once again;
(h) slowly withdrawing the plunger 7 from the specimen container 1 until all the urine is in the tip 4 and the space 3, located above this, of the specimen container 1;
(i) completely withdrawing the plunger 7 from the specimen container 1 and discarding the plunger;
(k) sealing the specimen container 1 at the top by means of the stopper 35;
(l) turning the specimen container 1 around and ventilating the inner space by removing the sealing cap;
(m) turning the specimen container 1 around again with the tip 4 downwards, guiding the tip 4 over the chamber in a slide;
(n) exerting a light and short pressure on the middle of the stopper 35 to empty into the counting chamber an amount of urine sufficient to fill the latter.

I claim:

1. A device for urinalysis comprising:
(a) a cylindrical specimen container of a transparent material, of which a top end during use is open and is sealable in a leakproof manner by a stopper, and of which a bottom end is tapered in a funnel shape and i s connected to a pipette tip;
(b) a stopper with an elastically deformable end wall for sealing said top end of the specimen container;
(c) a sealing cap for attachment to the pipette tip to sea said tip in a leakproof manner;
(d) a tubular, cylindrical plunger of a transparent material for slideable insertion in liquid-tight and gas-tight relationship into the specimen container, and of which a top, open end is sealable in a leakproof manner by said stopper, and of which a bottom end is sealable by a two part upper filter arrangement separated from a third filter by a lower backflush chamber;
(e) a 10 ml measuring mark on a circumference of the specimen container; and
(f) a cylinder of a transparent material arranged inside the plunger and connected in a leakproof manner to said upper filter arrangement to form an upper backflush chamber; and wherein said cylinder is sealed at its top by an end wall having a fine center bore.

2. The device according to claim 1, wherein a disc projects radially outwards from the pipette tip of the specimen container and said sealing cap is provided with a rolled -on closure which, when pushed onto the pipette tip turns inwards to clamp the sealing cap on the disc.

3. The device according to claim 1, wherein said upper filter arrangement has two filters connected in series and said two filters are of different pore sizes.

4. The device according to claim 3, wherein said third filter is of larger pore sizes than said upper filters.

5. The device according to claim 4 wherein there is a cylindrical tube support which forms said lower backflush chamber.

* * * * *